United States Patent
Rossignol et al.

(10) Patent No.: US 10,247,715 B2
(45) Date of Patent: Apr. 2, 2019

(54) SENSOR AND DEVICE FOR DETECTING AN ANALYTE IN A LIQUID

(71) Applicants: UNIVERSITE DE BOURGOGNE, Dijon (FR); INSTITUT NATIONAL SUPERIEUR DES SCIENCES AGRONOMIQUES DE L'ALIMENTATION ET DE L'ENVIRONNEMENT, Dijon (FR)

(72) Inventors: Jerome Rossignol, Dijon (FR); Elias Bou-Maroun, St Apollinaire (FR); Celine Lafarge, Dijon (FR); Didier Stuerga, Dijon (FR); Philippe Cayot, Mirebeau sur Beze (FR)

(73) Assignees: Universite De Bourgogne (FR); Institut National Superieur Des Sciences Agronomiques De L'alimentation Et De L'environnement (FR)

( * ) Notice: Subject to any disclaimer, the term of this patent is extended or adjusted under 35 U.S.C. 154(b) by 1 day.

(21) Appl. No.: 15/327,282

(22) PCT Filed: Jun. 25, 2015

(86) PCT No.: PCT/FR2015/051717
§ 371 (c)(1),
(2) Date: Jan. 18, 2017

(87) PCT Pub. No.: WO2016/012682
PCT Pub. Date: Jan. 28, 2016

(65) Prior Publication Data
US 2017/0160254 A1 Jun. 8, 2017

(30) Foreign Application Priority Data
Jul. 25, 2014 (FR) .................... 14 57204

(51) Int. Cl.
*G01N 33/14* (2006.01)
*A61B 5/05* (2006.01)
*G01N 22/00* (2006.01)

(52) U.S. Cl.
CPC ......... *G01N 33/146* (2013.01); *A61B 5/0507* (2013.01); *G01N 22/00* (2013.01); *G01N 2600/00* (2013.01)

(58) Field of Classification Search
CPC ... G01N 33/146; G01N 22/00; G01N 2600/00
(Continued)

(56) References Cited

U.S. PATENT DOCUMENTS

| 6,310,110 B1* | 10/2001 | Markowitz | B01J 37/00 210/656 |
| 2003/0129092 A1* | 7/2003 | Murray | B01J 20/268 422/82.07 |

(Continued)

FOREIGN PATENT DOCUMENTS

JP 2001036332 A 2/2001

OTHER PUBLICATIONS

Haupt, K. et al. (2000). "Molecularly Imprinted Polymers and Their Use in Biomimetic Sensors." Chem. Rev. 100(7): 2495-2504.*
(Continued)

*Primary Examiner* — Jill A Warden
*Assistant Examiner* — Dwayne K Handy
(74) *Attorney, Agent, or Firm* — Forge IP, PLLC

(57) ABSTRACT

A sensor for detecting an analyte in a liquid. The sensor includes an antenna, covered with a layer of a molecularly imprinted polymer capable of interacting with an analyte and inducing a variation in the characteristics of the antenna within the microwave frequency range.

10 Claims, 3 Drawing Sheets

(58) Field of Classification Search
USPC .................................................. 422/82.02
See application file for complete search history.

(56) References Cited

U.S. PATENT DOCUMENTS

| | | |
|---|---|---|
| 2004/0126814 A1 | 7/2004 | Singh et al. |
| 2008/0144002 A1 | 6/2008 | Murray et al. |
| 2010/0047919 A1* | 2/2010 | Klunder .......... G01N 33/54373 436/172 |
| 2012/0100358 A1* | 4/2012 | Haupt ................... B01J 20/268 428/220 |
| 2012/0288944 A1 | 11/2012 | Murray et al. |
| 2013/0303868 A1* | 11/2013 | Fischer ................ A61B 5/0507 600/364 |

OTHER PUBLICATIONS

Abduljabar, A. (2014). "Novel Microwave Microfluidic Sensor Using a Microstrip Split-Ring Resonator." IEEETransactions on Microwave Theory and Tech. 62:3. 679-688. (Year: 2014).*
Haupt, K. et al, "Molecularly Imprinted Polymers and Their Use in Biomimetic Sensors", Chemical Reviews, American Chemical Society, US, vol. 100, No. 7, Jul. 12, 2000, pp. 2495-2504.
Mccann, Donald F. et al, "Novel transducer configurations for bulk acoustic wave sensors", 2008 IEEE Sensors, Lecce, Ital, IEEE, Piscataway, NJ, USA, Oct. 26, 2008, pp. 1448-1451.
Percival C J et al, "Molecular-Imprinted, Polymer-Coated Quartz Crystal Microbalances for the Detection of Terpenes", Analytical Chemistry, American Chemical Society, US, vol. 73, No. 17, Sep. 1, 2001, pp. 4225-4228.
Wolff, Ulrich et al, "SAW sensors for harsh environments", IEEE Sensors Journal, IEEE Service Center, New York, NY, US, vol. 1, No. 1, Jun. 1, 2001, pp. 4-13.

* cited by examiner

SENSOR AND DEVICE FOR DETECTING AN ANALYTE IN A LIQUID

FIELD OF THE INVENTION

This invention concerns a microwave transduction sensor consisting of a "Molecularly Imprinted Polymer" (MIP) as a sensitive material, and more specifically molecularly imprinted material based on silica, called "Molecularly Imprinted Silica" or MIS. The invention also concerns a device for detecting an analyte in a liquid. The invention is particularly advantageous when applied to detecting a fungicide such as iprodione in a hydro-alcoholic medium.

BACKGROUND OF THE INVENTION

In the field of analytical chemistry in particular, various means are well known for analyzing liquids such as water or wine, for example to determine, in particular, the chemical content of said liquids, and more specifically to determine whether pollutants such as fungicides are present.

Test strips or chromatography are among the systems which are most commonly used.

Test strips do not allow traces of fungicides to be detected at the level of several ng/l, and the disadvantage of chromatography is that it can take a long time and it be costly.

The most commonly used method for measuring fungicides is high-performance liquid chromatography or HPLC. However this analysis requires numerous preliminary operations consisting of extraction, purification, concentration and potentially drying steps.

Other newer methods have been used to avoid the sample treatment step (extraction, purification, concentration and drying) in order to reduce the analysis time and to reduce the significant quantities of solvent used for extraction.

We can cite the example of fiber from Solid Phase Micro Extraction or SPME. This method is based on using a 110 µm silica fiber coated with a 7 to 100 µm thick adsorbent over a length of 1 cm and located at the end of a syringe. The needle pierces the septum of the vial containing the sample and the fiber is immersed within the sample for the extraction of compounds. The fiber is introduced into a chromatograph in gas phase after a given extraction period (Pichon V, 2012). Extraction sur phase solide pour l'analyse de composés organiques [Extraction in solid phase for the analysis of organic compounds] [P 1420]. Techniques de l'Ingénieur, base documentaire Chromatographie et techniques séparatives [Engineering techniques, chromatography document base and separating techniques].

The SPME fiber requires several steps to be implemented before the fungicide can be determined: ten-minute extraction followed by a chromatographic analysis which lasts at least 30 minutes.

We are also aware of sensors consisting of "molecularly imprinted polymer" or MIP. This includes the American patent applications US 2008/0144002, US 2012/0288944, US 2004/0126814 and the scientific publication "Molecular-Imprinted, Polymer-Coated Quartz Crystal Microbalances for the Detection of Terpenes (Anal. Chem. 2001; 73 4225-4228). In this specific case, transduction is performed using an acoustic sensor within the sensitive material.

Document US 2008/0288944 describes a sensor consisting of a molecularly imprinted polymer for the detection of a specific targeted inorganic ion. This sensor consists of one or more molecularly imprinted polymer beads with a macro-porous structure containing a plurality of cavities called complexation, said cavities contain cationic ligands which are spatially oriented in order to selectively receive and bind to a specific targeted inorganic ion intended for detection. The sensor, associated with a light source such as an ultraviolet, infrared or visible light, allows the luminescence of the molecularly imprinted polymer beads to which a particular targeted inorganic ion is fixed to be obtained.

Document US 2012/0288944 describes a procedure for detecting a tracer molecular structure in a fluid using a sensor consisting of a molecularly imprinted polymer. The procedure consists of placing a molecularly imprinted polymer in a crosslinked star into contact with the fluid, then correlating the change of color in the fluid with the quantity of the tracer molecular structure within the fluid. The device has polymeric arms attached to a core, and the core has molecular-size cavities suitable for selectively receiving and binding molecules with a tracer molecular structure, said core also has a colorimetric indicator. The movement molecule is selectively removed from the molecularly imprinted crosslinked polymer by exposure to the tracer molecular structure within the fluid, therefore indicating the presence of the tracer molecular structure within the fluid based on the loss of color.

Document US 2004/0126814 describes a sensor for the detection of a target analyte using a molecularly imprinted polymer (MIP) imprinted with a target analyte. The MIP can be used as a working electrode in electrochemical impedance spectroscopy, either by coating a substrate or by being pressed onto a disk. The sensor can also use the molecularly imprinted polymer (MIP) to detect a target analyte using other electrochemical procedures.

The scientific publication "Molecular-Imprinted, Polymer-Coated Quartz Crystal Microbalances for the Detection of Terpenes (Anal. Chem. 2001, 73, 4225-4228) describes a quartz microbalance which allows terpenes to be detected. The microbalance is made from two conductive electrodes with a piezoelectric substrate on both sides covered with a molecularly imprinted polymer layer. When an electrical current is applied, quartz located between the two electrodes on the substrate vibrates producing an acoustic wave through the sensitive material. However this quartz can only oscillate at one frequency when current is applied to its terminals. The current in the electrode terminals can be transmitted in an undesired way to the quartz terminals, for example by salt crystal conduction in a liquid which causes false detection of terpenes. Furthermore, this device only allows one single measurement to be made indicating the presence or absence of terpene, and does not allow the presence of terpenes to be quantified.

The invention's technical problem therefore consists of proposing a device for the detection of an analyte in a liquid allowing the presence of an analyte to be detected in a liquid in a rapid and reliable manner.

SUMMARY OF THE INVENTION

The invention responds to this technical problem by means of an antenna whose characteristics change in the presence of an analyte using a molecularly imprinted polymer.

For this purpose, according to a first feature, the invention concerns a sensor for the detection of an analyte in a liquid with an antenna formed by:
   a substrate consisting of two opposite faces,
   a ground plane on a first face of a substrate, and
   at least one metallic part on a second face of the substrate,
   at least one part of the second face of the substrate being covered with a molecularly imprinted polymer layer which is capable of interacting with an analyte and producing a variation in the antenna characteristics within the microwave frequency range.

The invention therefore allows the presence of an analyte in a liquid to be quickly detected using a signal transmitted to the antenna then reflected by the antenna. Measuring the ratio of the signal reflected by the antenna to a reference signal allows variations in the characteristics of the antenna, caused by the detection of the analyte by the molecularly imprinted polymer, to be estimated. When the reflected signal corresponds to the reference signal, this indicates that no analyte is detected. When the signal reflected differs from the reference signal, this indicates the detection of an analyte. Furthermore, the difference between the reflected signal and the reference signal allows the presence of the analyte to be quantified.

The reliability of the measurement performed by the invention is improved by the type of signal reflected by the antenna which consists of two components that vary in the presence of an analyte: an amplitude and a phase shift. These two components of the reflected signal can be measured independently in order to estimate the characteristics of the antenna such as the gain or the quality factor. These antenna characteristics allow the measurement concerning the detection or quantification of the analyte to be confirmed and limit measurement errors. Furthermore, the frequency of the signal transmitted by the antenna, and therefore the reflected signal, can be varied in order to carry out several consecutive measurements and confirm the presence and/or quantity of the analyte.

According to one operating procedure, the molecularly imprinted polymer layer is formed on a silica or acrylate base.

According to one operating procedure, the molecularly imprinted polymer layer has a thickness between 50 nm and 1 μm.

According to one operating procedure, the molecularly imprinted polymer layer is synthesized by a sol-gel process using alkoxysilane when the molecularly imprinted polymer layer is made from a silica base and the molecularly imprinted polymer layer is synthesized by radical polymerization when the molecularly imprinted polymer layer is made from an acrylate base.

According to one operating procedure, the metallic part consists of three internal strips forming an isosceles triangle and two external strips which extend symmetrically from two corners of the isosceles triangle with respect to the median extending through the free corner.

According to one operating procedure, the ground plane also extends along the first face of the substrate, and the external strips are capable of linking the ground plane on the first face of the substrate to the internal strips.

According to one operating procedure, the free corner is electrically connected to a connector capable of collecting the antenna characteristics within the microwave frequency range.

According to one operating procedure, the length of each metallic strip is equal to $\lambda/2$, with $\lambda$ being the length of the wave predetermined at the antenna.

According to one operating procedure, the length of the wave which is predetermined at the antenna is between 1 GHz and 10 GHz.

According to a second feature, the invention concerns a device for detecting at least one analyte in a liquid including at least one sensor in accordance with the first feature of the invention, means of emission of an electromagnetic wave at a frequency between 300 MHz and 300 GHz, means to receive the wave reflected onto the sensor and means of measurement for the ratio between the reflected wave and the incident wave according to the frequency.

Advantageously, the means of emission of an electromagnetic wave and the means to receive the reflected wave consist of a vector network analyzer.

BRIEF DESCRIPTION OF THE FIGURES

Further advantages and features will become clearer from the following description of one operating variation, given by way of a non-limiting example, of the device for detecting fungicides in a hydro-alcoholic environment in accordance with the invention, with reference to the accompanying drawings in which.

DETAILED DESCRIPTION OF THE INVENTION

In the continuation of the description of the device for detecting an analyte in a liquid in accordance with the invention, the same numerical references designate the same parts. According to the invention, the device is specifically intended to detect fungicides such as iprodione in wine; however, it is quite obvious that the device according to the invention can find many applications such as detecting fungicides in water without departing from the scope of the invention. For example, as part of this invention, the analytes which can be detected belong to the family of microorganisms such as viruses, bacteria, molds or to the family of biologically active organic molecules such as pesticides, toxins, endocrine disruptors, hormones, enzymes, vitamins, antibiotics, and medicines; or the family of ions such as essential minerals, toxic metals, organic acids or organic bases; or the family of biomolecules such as lipids and their derivatives, amino acids and their derivatives, peptides and their derivatives, proteins and their derivatives, proteins and their derivatives, one chain carbohydrates without branching and their derivatives, and saccharides and their derivatives.

Figure 1:
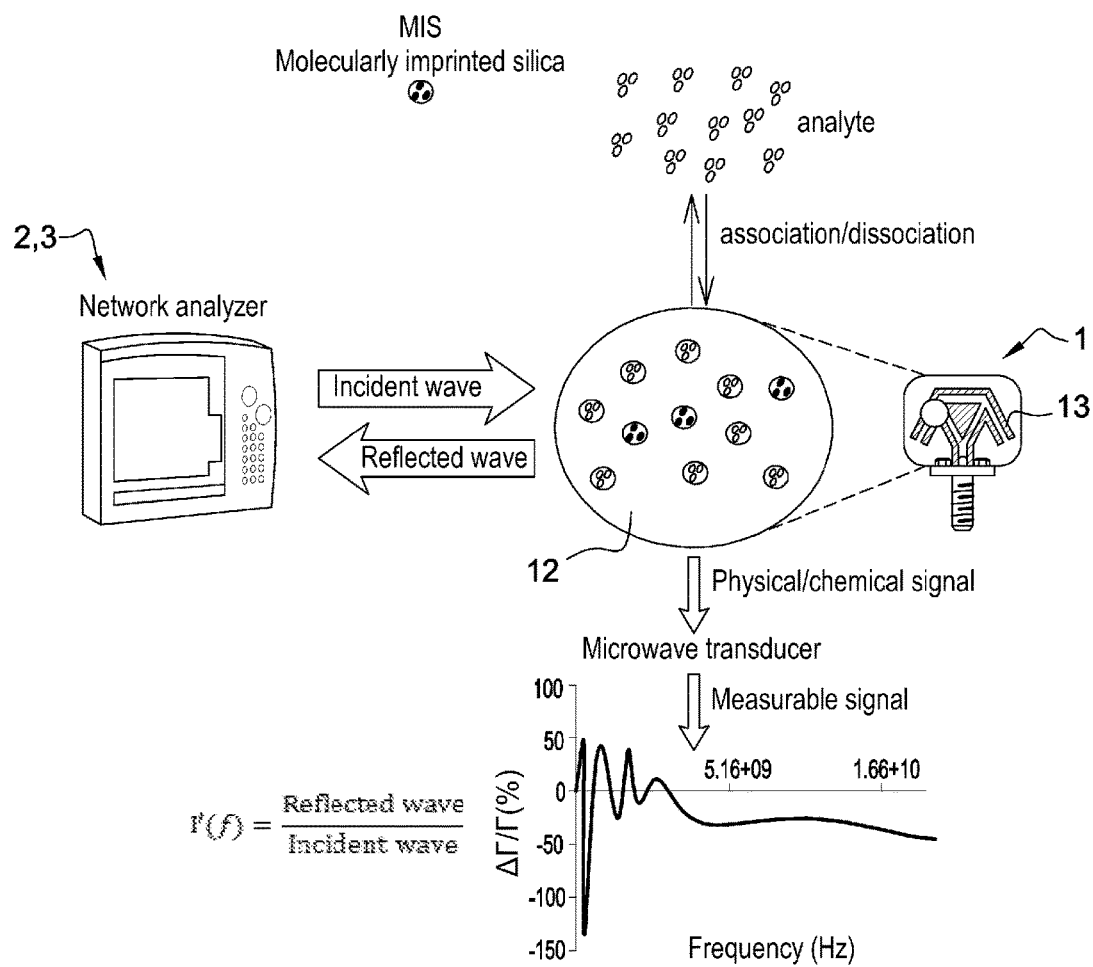
FIG. 1 is a schematic diagram of the device according to one operating procedure of the invention.
Figure 2:
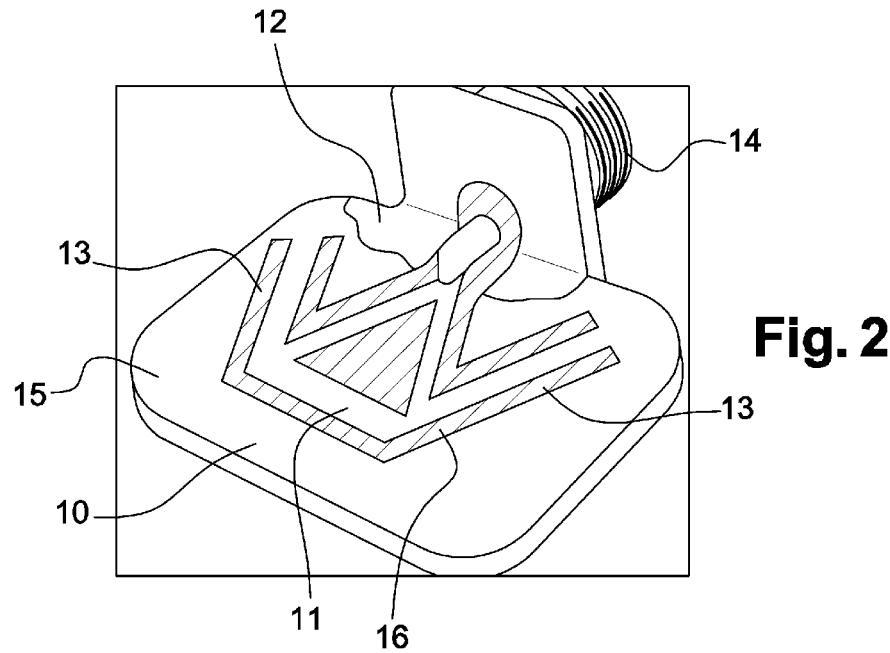
FIG. 2 is a view of the top of the sensor from FIG. 1, and has a partially represented molecularly imprinted polymer layer.
Figure 3:
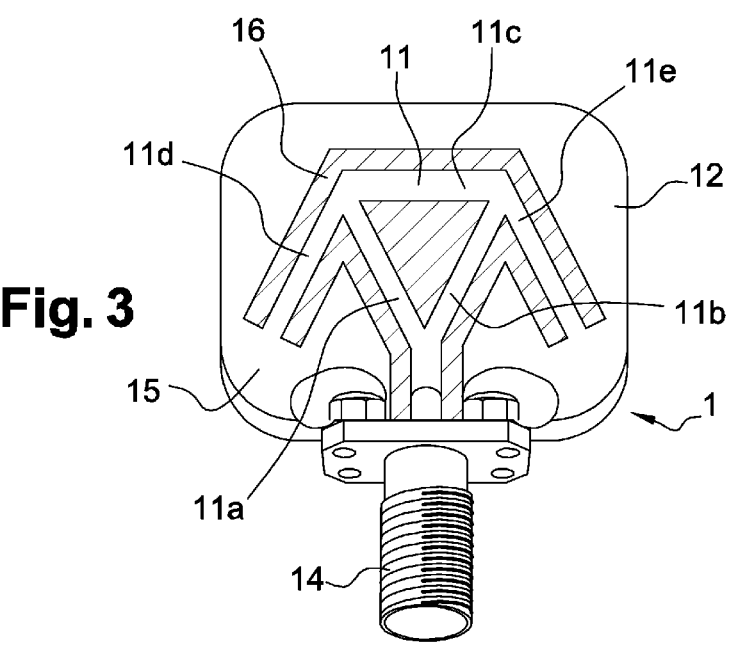
FIG. 3 is a view of the top of the sensor from FIG. 1.

In reference to FIG. 1, the device consists of a sensor (1), a means of emission (2) of an electromagnetic wave at a frequency between 300 MHz and 300 GHz, more specifically between 1 and 10 GHz, means to receive (3) the wave reflected onto the sensor (1) which is immersed into a hydro-alcoholic liquid which includes at least one analyte to be detected, said analyte is for example a fungicide such as iprodione, and means of measurement of the ratio between the reflected wave and the incident wave according to the frequency. The aforesaid means of emission (2) of an electromagnetic wave and the means to receive (3) the reflected wave consist of a vector network analyzer. Furthermore, in reference to FIGS. 1 to 3, the sensor (1) consists of an antenna (13) made from at least one substrate (10) including, on at least one of its faces, a ground plane (15) and, on the other face, at least one metallic part (11), with the said substrate (10) and said metallic part (11) covered with a layer (12) of a molecularly imprinted polymer. The aforesaid molecularly imprinted polymer is preferably made from a silica base called MIS, "Molecularly Imprinted Silica". The aforesaid molecularly imprinted polymer layer (12) has a constant thickness to within a micrometer, between 1 nm and 100 μm and preferably between 50 nm and 1 μm. The molecularly imprinted polymer layer (12) is preferably synthesized by means of a sol-gel procedure based on alcoxysilane. Additionally, the substrate (10) consists of a glass strip. In this particular example of operation, the aforesaid strip has a slightly rectangular or square form and the ground plane (15) also covers a part of the face including the metallic part (11).

It is quite obvious that the strip can have any form without having to departing from the scope of the invention. Additionally, the ground plane (15) may be arranged on only one face of the antenna (13) opposite the face bearing the metallic part (11). The molecularly imprinted polymer layer (12) may also be made on the basis of another polymer, such as acrylate, without changing the innovation. The molecularly imprinted polymers based on acrylate are synthesized by means of radical polymerization. The molecularly imprinted polymer layer (12) may only cover part of the antenna face (13) which includes the metallic part (11).

Additionally, the metallic part (11) has a particularly advantageous form including three internal strips (11a-11c) and two external strips (11d-11e). Preferably, the metallic part (11) is made from silver but another conductive material may be used without changing the invention. The three internal strips (11a-11c) form an insulated surface (16) in the shape of an isosceles triangle. The internal strips (11a-11c) are electrically insulated from the ground plane (15) which is arranged on the face containing the metallic part (11) by an insulating surface (16). One corner of the isosceles triangle, called the free corner, is linked to a connector (14) to supply the metallic part (11) from the connector (14) and to collect the antenna characteristics (13) within the microwave frequency range. For example, the connector (14) may be a standard SMA-type baseplate. The two other corners of the isosceles triangle are respectively linked to the external strips (11d-11e). The external strips (11d-11e) have two edges, one edge electrically connected to the ground plate (15) and one edge electrically connected to the internal strips (11a-11c). The external strips (11d-11e) are also electrically insulated from the ground plane (15) which is arranged on the face containing the metallic part (11) by an insulating surface (16) and extends symmetrically with reference to the median extending through the free corner. The insulating surface (16) is represented by hatching on FIGS. 1 to 3. The length of each metallic strip (11a-11e) is preferably equal to $\lambda/2$, with $\lambda$ being the length of the wave which is predetermined at the antenna (13) within the microwave frequency range. For example, the wave length $\lambda$ can be determined such that the antenna (13) has a resonant frequency between 1 GHz and 10 GHz, preferably 2.4 GHz. As a variant, the lengths of each strip (11a-11e) can be equal to $\lambda$ or $3\lambda/2$ without changing the invention and the antenna resonant frequency (13) may vary.

The antenna (13) may, of course, have any form. Additionally, it is quite obvious that the sensor (1) can have several antennae (13) of any form without departing from the scope of the invention.

The sensor manufacturing procedure (1) includes a step of cutting the substrate (10), with glass, into the form of a rectangular strip of around 2 cm by 3 cm before a mechanical polishing step. Said glass strip is then covered by a silver layer 20 to 30 μm thick. Said silver-covered strip is then polished several times until a silver poly mirror is obtained, then an ultra-violet (UV) sensitive resin is deposited by a procedure called "spin-coating" which is well known to a person skilled in the art. A mask, representing the geometry of the antenna (13), is then placed on the resin, the strip is then radiated with ultra-violet (UV) light. After exposing the resin, a silver wet-etch is made and the remaining resin is removed by any appropriate means which are well-known to an expert skilled in the art. After rinsing with distilled water, the sensor (1) may be polished and cleaned again in a step to remove any imperfections. Furthermore, the sensor (1) is covered in a molecularly imprinted polymer layer which is elaborated with the target analyte present, for example iprodione. Lastly, the sensor (1) is then equipped with an SMA-type connector (14) ("Subminiature version A") which is made from a coaxial connector with an impedance of 50 Ohms which is welded or not welded to the sensor (1).

The molecularly imprinted polymer is synthesized from a silica base (MIS) using the following selected ratio 1/4/59 (ratio of iprodione/monomers/reticulating agent). The monomer APTMS (3-aminopropyltrimethoxysilane) is used. It was synthesized in the following way:

i) 16.8 ml of pure ethanol was placed in a water bath at 40° C. for 10 min.
ii) 0.08 g of iprodione was added, then 2 ml of water.
iii) 0.18 ml of a monomer (APTMS) was then added, the samples were then stirred for 5 min.
iv) 3.1 ml of TEOS (tetraethyl orthosilicate) crosslinking agent was added and the samples were then stirred again for 5 minutes.
v) 1 ml of an initiator (ammonium hydroxide) was then added, the samples were then stirred for 5 min.
vi) The samples were then placed in a water bath (40° C.) for 24 h and stirred.
vii) The precipitate obtained was then separated from the liquid phase by centrifugation at 7500 RPM (10000 G) for 10 min. at 20° C. Several ethanol washes were successively made until there was no more iprodione in the washing water during the HPLC analysis. The polymer was then placed in the sterilizer at 60° C. for 24 hours following the various washes.

As a variation, a non-imprinted polymer, or an NIS, can be synthesized following the same protocol as the MIS by not adding iprodione in the middle of the synthesis. The MIS or NIS was deposited on the sensor in the form of a suspension. Powder PVC (Polyvinyl chloride) was added to a suspension of MIS in the THF (tetrahydrofuran) by respecting the following ratio to do this: 25/8/4, MIS (mg)/PVC (mg)/THF (mL).

The solution prepared in this way was then deposited on the surface of the sensor (1) by a spin-coating method by using the following parameters: speed=1,000 rpm, acceleration 4,000 rpm, duration=40 s. The molecularly imprinted polymer can be deposited on the sensor by chemical functionalization of the substrate without departing from the scope of the invention. Several polymer-imprinted polymers can be deposited on the same sensor without departing from the scope of the invention.

Thus, when the sensor (1) is immersed into a liquid containing the target analyte, for example iprodione, the vector network analyzer emits an electromagnetic wave at an excitation frequency, within the microwave range, and evaluates the wave reflected upon entry thereof. The waves emitted and reflected are transmitted through the connector (14). The interaction of the analyte with the molecularly imprinted material of the sensor (1) leads to variations in the characteristics of the antenna (13) within the microwave range. The molecularly imprinted material involving a propagative microwave structure has its variation of dielectric properties enhanced by the geometry of the antenna (13). For each excitation frequency, the reflected wave/incident wave ratio is associated with the interaction of the molecularly imprinted material with the analyte in this way. The network analyzer emits several frequencies of the order of a thousand in the range of 1 to 10 GHz obtaining a signature called a microwave describing the interaction of the molecularly imprinted material with the analyte.

Figure 4:
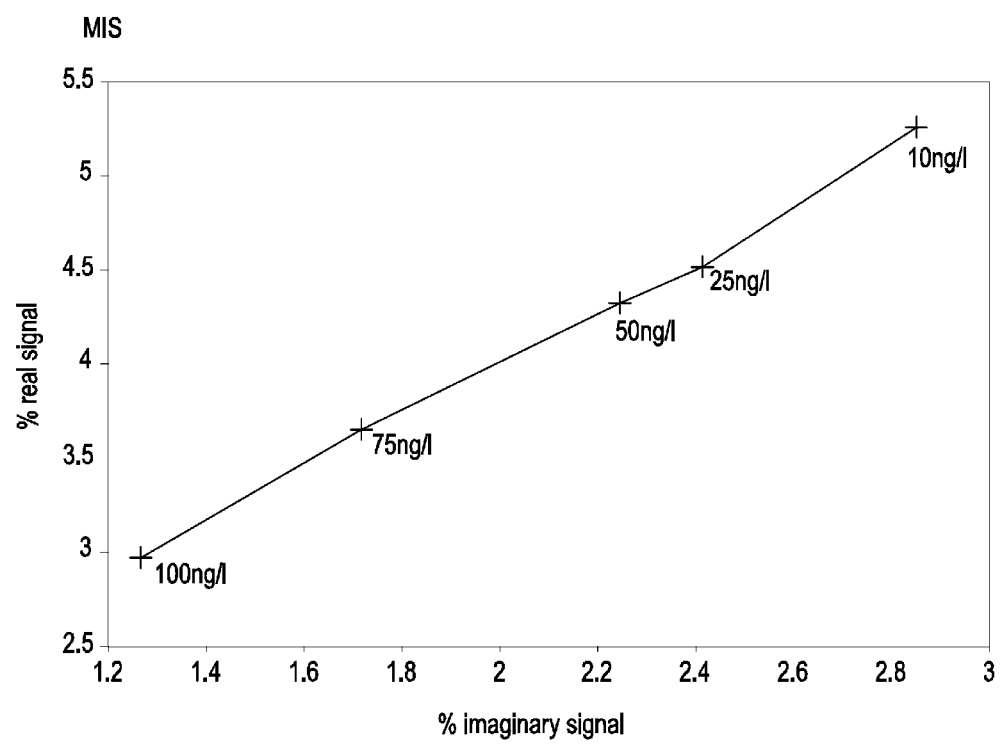
FIG. 4 is a graphic representation of the transformation of the antenna characteristics of the sensor in FIG. 1 at the resonant frequency of the antenna according to the quantity of the analyte.

In reference to FIG. 4, the response of the sensor (1) in accordance with the invention is represented, at the resonant frequency 2.4 GHz, in the presence of several quantities of the analyte. For each quantity of the analyte, the variation of amplitude and phase shift of the signal received with respect to a reference signal allows two complementary measurements of the antenna characteristics (13) called the real and imaginary parts to be supplied. FIG. 4 illustrates the transformation of this real part according to the imaginary part. This slightly linear transformation therefore allows the concentration of the analyte within the liquid to be extrapolated from the estimation of the real part and the imaginary part of each measurement. We note that each measurement is taken in around a minute.

Lastly, it is clear that the examples that have just been given are only specific illustrations and by no means limiting as concerns the scope of the invention.

The invention claimed is:

1. A device for detecting at least one analyte in a liquid, the device comprising:
    a sensor having an antenna including:
        a substrate comprising first and second opposite faces,
        a ground plane arranged on the first face of the substrate, and
        at least one metallic part located on the second face of the substrate, at least some of the metallic part covered with a molecularly imprinted polymer layer comprising a silica or acrylate base that interacts with an analyte to produce a variation in the antenna characteristics within the microwave frequency range;
    wherein the metallic part comprises three internal strips forming an isosceles triangle and two external strips which extend symmetrically from first and second corners of the isosceles triangle with respect to the median extending through a third corner of the isosceles triangle; and
    a vector network analyzer that emits an electromagnetic wave at a frequency between 300 MHz and 300 GHz, the vector network analyzer emitting an incident wave to the antenna, receiving a reflected wave from the antenna, and measuring the ratio between the reflected wave and the incident wave as a function of frequency.

2. The device according to claim 1, further comprising a connector linked to the antenna and the network analyzer, such that the incident and reflected waves are transmitted between the antenna and the network analyzer through the connector.

3. The device according to claim 2, wherein the connector is linked to the metallic part of the antenna.

4. The device according to claim 1, wherein the molecularly imprinted polymer layer has a thickness between 50 nm and 1 µm.

5. The device according to claim 1, wherein the molecularly imprinted polymer layer is made from a silica base, and the molecularly imprinted polymer layer is synthesized by a sol-gel process using alkoxysilane.

6. The device according to claim 1, wherein the molecularly imprinted polymer layer is made from an acrylate base, and the molecularly imprinted polymer layer is synthesized by radical polymerization.

7. The device according to claim 1, wherein the ground plane also extends along the first face of the substrate, and the external strips link the ground plane on the first face of the substrate to the internal strips.

8. The device according to claim 1, wherein the third corner is electrically connected to a connector that collects the antenna characteristics within the microwave frequency range.

9. The device according to claim 1, wherein the length of each metallic strip of the metallic part is equal to $\lambda/2$, with $\lambda$ being the length of the wave predetermined at the antenna.

10. The device according to claim 8, wherein the length of the wave predetermined at the antenna is between 1 GHz and 10 GHz.

* * * * *